(12) United States Patent
Siegler et al.

(10) Patent No.: US 8,683,612 B2
(45) Date of Patent: *Apr. 1, 2014

(54) CERVICAL SPINE PROTECTION APPARATUS AND METHODS OF USE

(71) Applicants: Sorin Siegler, Merion Station, PA (US); Mary Milone, Philadelphia, PA (US); Yoganand Ghati, Chester Springs, PA (US)

(72) Inventors: Sorin Siegler, Merion Station, PA (US); Mary Milone, Philadelphia, PA (US); Yoganand Ghati, Chester Springs, PA (US)

(73) Assignee: Drexel University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/957,726

(22) Filed: Aug. 2, 2013

(65) Prior Publication Data

US 2013/0317403 A1 Nov. 28, 2013

Related U.S. Application Data

(63) Continuation of application No. 13/690,598, filed on Nov. 30, 2012, now Pat. No. 8,528,113, which is a continuation of application No. 12/879,321, filed on Sep. 10, 2010, now Pat. No. 8,341,770.

(60) Provisional application No. 61/241,204, filed on Sep. 10, 2009.

(51) Int. Cl.
*F41H 1/04* (2006.01)
*A41D 13/05* (2006.01)

(52) U.S. Cl.
USPC .................. 2/6.8; 2/467; 2/468; 2/44; 2/410

(58) Field of Classification Search
USPC .............. 2/455, 459, 461, 410, 6.8, 411–416, 2/468, 44, 45, 421
See application file for complete search history.

(56) References Cited

U.S. PATENT DOCUMENTS

| | | |
|---|---|---|
| 3,671,974 A | 6/1972 | Sims |
| 3,818,509 A | 6/1974 | Romo et al. |
| 3,900,896 A | 8/1975 | Ackerman |
| 4,219,193 A | 8/1980 | Newman |
| 4,319,362 A | 3/1982 | Ettinger |
| 4,426,908 A | 1/1984 | Ullmann |
| 4,638,510 A | 1/1987 | Hubbard |
| 4,870,705 A | 10/1989 | Higby |

(Continued)

FOREIGN PATENT DOCUMENTS

EP 1649903 A1 4/2006

OTHER PUBLICATIONS

Siegler, "Effect of additional mass on head position and neck muscle fatigue and the use of a cervical spine protective device to reduce the effects," Annual Soc. for Neuroescience Conf., Nov. 15, 2008.

*Primary Examiner* — Bobby Muromoto, Jr.
(74) *Attorney, Agent, or Firm* — Mendelsohn, Drucker & Dunleavy, P.C.

(57) ABSTRACT

The invention is directed to a cervical spine protection apparatus one or more composite bands attached to provide restraint of one or more motions of the cervical spine of a wearer. The apparatus is designed to protect a wearer from incurring cervical spinal injuries, and/or to reduce the severity of cervical spine injuries without substantially compromising the normal functional range of motion of the wearer's cervical spine.

21 Claims, 15 Drawing Sheets

(56) References Cited

U.S. PATENT DOCUMENTS

| | | |
|---|---|---|
| 5,123,408 A | 6/1992 | Gaines |
| 5,205,803 A | 4/1993 | Zemitis |
| 5,261,125 A | 11/1993 | Cartwright |
| 5,335,674 A | 8/1994 | Siegler |
| 5,336,139 A | 8/1994 | Miller |
| 5,371,905 A | 12/1994 | Keim |
| 5,404,590 A | 4/1995 | Monica |
| 5,437,613 A | 8/1995 | Reggio et al. |
| 5,483,698 A | 1/1996 | Douglas |
| 5,493,736 A | 2/1996 | Allison |
| 5,507,707 A | 4/1996 | Miller |
| 5,509,869 A | 4/1996 | Miller |
| 5,517,699 A | 5/1996 | Abraham |
| 5,815,846 A | 10/1998 | Calonge |
| 5,988,173 A | 11/1999 | Scruggs |
| 6,006,368 A | 12/1999 | Phillips |
| 6,202,263 B1 | 3/2001 | Harker |
| 6,298,483 B1 | 10/2001 | Schiebl |
| 6,385,781 B1 | 5/2002 | Rose |
| 6,810,535 B1 | 11/2004 | Moloney |
| 6,874,170 B1 | 4/2005 | Aaron |
| 6,886,186 B2 | 5/2005 | Jansen |
| 6,968,576 B2 | 11/2005 | McNeil |
| 6,971,123 B2 | 12/2005 | Weaver |
| 7,155,747 B2 | 1/2007 | Baker |
| 7,794,374 B1 | 9/2010 | Park |
| 7,797,764 B2 | 9/2010 | Norris |
| 8,046,846 B2 | 11/2011 | Karlsson et al. |
| 8,341,770 B2 * | 1/2013 | Siegler et al. ............ 2/411 |
| 2007/0155600 A1 | 7/2007 | Cunningham et al. |
| 2008/0313791 A1 | 12/2008 | Nagely |
| 2010/0255964 A1 | 10/2010 | Wang |

* cited by examiner

FIGURE 6
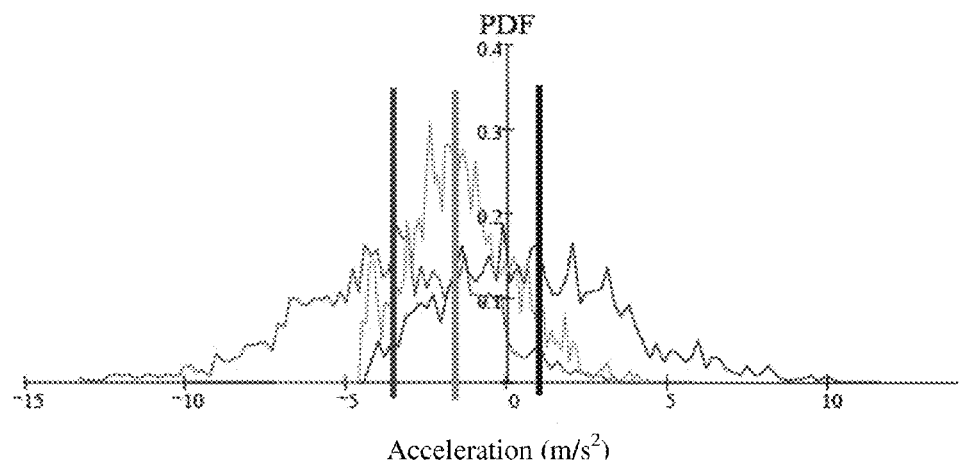
Acceleration (m/s²)
FIGURE 7(a)                                    FIGURE 7(b)
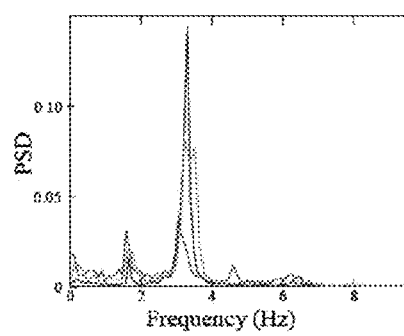 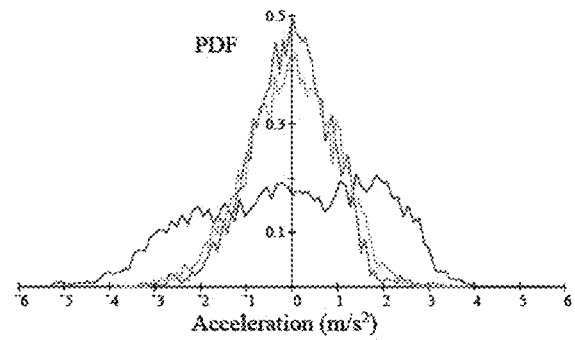
FIGURE 8
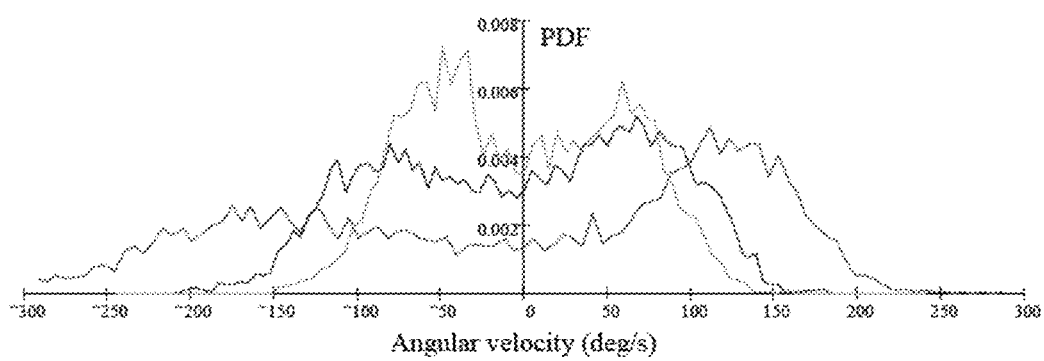

FIGURE 9(a)              FIGURE 9(b)              FIGURE 9(c)
Hybrid III 6-year-old dummy
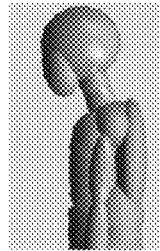 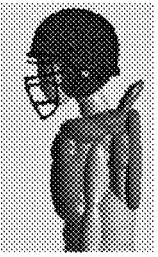 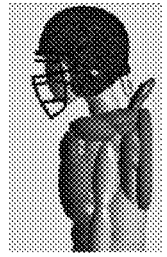
(a) With no protection    (b) with standard football protection    (c) with CSPD
Hybrid III 50th percentile male
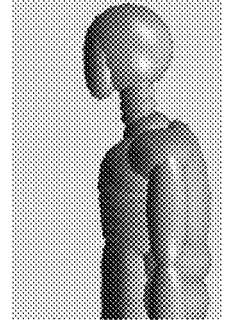 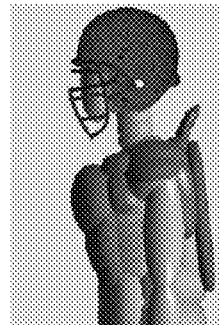 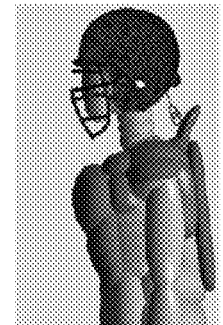
(a) With no protection    (b) with standard football protection    (c) with CSPD
FIGURE 9(d)              FIGURE 9(e)              FIGURES 9(f)
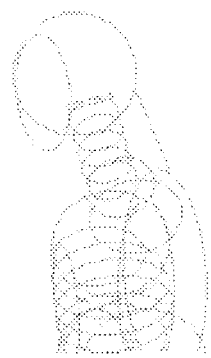 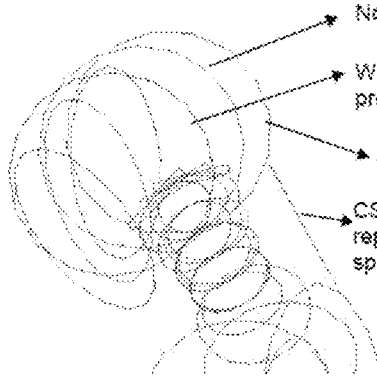
(a) Start of Simulation           (b) At instant of maximum flexion
FIGURE 10(a)                      FIGURE 10(b)

CERVICAL SPINE PROTECTION APPARATUS AND METHODS OF USE

BACKGROUND OF THE INVENTION

1. Field of the Invention

The invention is directed to a cervical spine protection apparatus and methods for use thereof. The invention may be useful for stabilizing the spine, particularly by facilitating the rehabilitation of or preventing and/or minimizing the occurrence and/or severity of spinal injuries, particularly cervical spine injuries.

2. Description of the Related Technology

High impact sports pose a substantial risk for head and spinal injuries. During a typical game of high school tackle football, about 40.5 head impacts occur per hour, and about 24.4 head impacts occur per hour during a typical game of high school hockey. Studies of helmet-to-helmet collisions in the National Football League (NFL) using hybrid III dummies found that during collision, an athlete's head experiences a change in velocity of about 7.2±18 m/s, a translational acceleration of about 94.3±27.5 g and a rotational acceleration of about 6432±1813 r/s$^2$ during impact. Although helmets offer some degree of protection for the head, they do not adequately safeguard the wearer from traumatic spinal injuries, particularly cervical spine injuries. To the contrary, the National Football Head and Neck Injury Registry concluded that helmets can increase the risk of neck injuries when athletes use the helmet as a weapon. For example, practices such as "spearing" can induce axial load tear drop fracture that may cause a wide range of neurological disorders, including quadriplegia. During 1945-2004, 497 deaths were caused by playing tackle football in the United States, 16% of which were attributed to spinal cord injuries; the annual incidence rate of permanent cervical spinal cord injuries was about 0.55 per 100,000 among tackle football players.

In general, injuries to the cervical spine may occur when impact or inertial forces acting on the head are large enough to deform the underlying connective tissues beyond their tolerance limits. When placed under extreme loading and functional demands induced by high impact sports, contortions of the soft tissue allow the cervical spine to assume injurious positions. The primary factors that contribute to neck injury are high torque jolts, the proximity of the neck to the anatomical joint limits, muscular fatigue and insufficiency, and the properties of the head mounted load. For example, cervical cord neurapraxia, which causes temporary paralysis as well as a radiating burning pain, numbness or tingling in the arm, is a common cervical spine injury incurred during high impact sports. Caused by traction injury to the brachial plexus, percussive injury to the upper trunk and/or nerve compression when the neck undergoes a combination of hyperextension and ipsilateral lateral rotation, cervical cord neurapraxia has a high incidence rate of 7 per 10,000 football participants and a high recurrence rate of about 56%. About 65% of college football players sustain at least one cervical cord neurapraxia injury during their college careers.

The risk of traumatic cervical spine injuries, such as cervical cord neurapraxia, is even higher in children and adolescents than adults. Due to the slower development of the cervical spine and the surrounding musculature relative to the anatomical development of the head, children and adolescents are more prone to cervical spine injuries. Additionally, the specific biomechanical characteristics of pediatric cervical spines increase the likelihood of incurring severe neurological damage.

Despite the overwhelming documented epidemiological evidence of the high incidence rate of cervical spine injuries caused by high impact sports, no apparatus currently exists to protect a user from incurring such injuries. Conventional neck protection devices, such as the cowboy collar, bullock collar, kerr collar and neck roll, are generally ineffective in protecting the wearer from a wide range of loading situations and neck injuries experienced by different players, such as quarterbacks and linemen, during football. Notably, these devices do not meet the performance requirements nor mitigate the risks associated with the various different positions in football. Furthermore, there is no means for customizing the device to the preference, physiological dimensions and biomechanics, or intended use of a wearer. Of these devices, experiments have shown that the cowboy collar is the only apparatus that has been found to be partially effective against hyper-extension of the neck. None of these devices, however, were effective in preventing other forms of forced movement, such as lateral bending or axial rotation. Furthermore, these devices tend to be bulky, substantially limit the natural range of motion of an athlete's head and interfere with athletic performance.

Additionally, neck exercisers and protectors that include conventional spring elements, such as that disclosed in U.S. Pat. No. 4,219,193, and head stabilizing systems incorporating hydraulic pistons, such as that disclosed in U.S. Pat. No. 6,968,576, are also inadequate in protecting against, or rehabilitating cervical spine injuries. The conventional spring and hydraulic mechanism of these devices fails to provide adequate resistance at the extreme ranges of motion of the cervical spine to prevent injury and also substantially interfere with and inhibit the wearer's range of motion. Additionally, the arrangement of the springs and dampening mechanisms of these patents are inadequate for protecting a wearer from a wide range of cervical spine injuries.

Therefore there is a need to develop a suitable apparatus capable of reducing the risk of a wide variety of cervical spine injuries by dynamically limiting the motion of the cervical spine to a functional and non-injurious range of motion without substantially limiting the wearer's normal range of motion.

SUMMARY OF THE INVENTION

The invention relates to a novel spine protection apparatus. In a first aspect, the apparatus includes a composite band having an elastic band with a modulus of elasticity of from about 20 psi to about 30,000 psi attached to a substantially non-extendable band with a modulus of elasticity of from about 400,000 psi to about 7,500,000 psi, wherein when the composite band is at rest, there is sufficient slack in the substantially non-extendable band to permit the elastic band to stretch a distance which defines a range of motion for a wearer of said composite band.

The invention is also directed to a method for spinal stabilization involving the steps of: providing at least one composite band having an elastic band with a modulus of elasticity of from about 20 psi to about 30,000 psi attached to a substantially non-extendable band with a modulus of elasticity of from about 400,000 psi to about 7,500,000 psi; attaching the composite band to first and second attachment structures located at different positions along a spine in a manner whereby when the composite band is at rest, there is sufficient slack in the substantially non-extendable band to permit the elastic band to stretch a distance which defines a range of motion along a longitudinal axis of the elastic band for a wearer of the composite band.

BRIEF DESCRIPTION OF THE DRAWINGS

FIG. 6 is graph of the amplitude distribution as a function of distance for the positions of the cervical spine in the sagittal plane for an individual running on a treadmill who was unprotected, wearing football gear, and the same individual wearing both football gear and an exemplary cervical spine protection apparatus of the present invention; mean values are represented by vertical lines.

FIG. 7(a) is a graph of power spectral density as a function of frequency for an individual who was unprotected, wearing football gear, and the same individual wearing both football gear and an exemplary cervical spine protection apparatus of the present invention.

FIG. 7(b) is a graph of the amplitude distribution of the linear acceleration of an individual's trunk along the x-axis from the posterior to anterior for an individual who was unprotected, wearing football gear, and the same individual wearing both football gear and an exemplary cervical spine protection apparatus of the present invention.

FIG. 8 is a graph of the amplitude distribution of the cervical spine pitch velocity for an individual who was unprotected, wearing football gear, and the same individual wearing both football gear and an exemplary cervical spine protection apparatus of the present invention.

FIG. 9(a) is a schematic diagram of a hybrid III dummy representing a 6 year old male child with no cervical spine protection.

FIG. 9(b) is a schematic diagram of a hybrid III dummy representing a 6 year old male child wearing football gear.

FIG. 9(c) is a schematic diagram of a hybrid III dummy representing a 6 year old male child wearing football gear and an exemplary cervical spine protection apparatus of the present invention.

FIG. 9(d) is a schematic diagram of a hybrid III dummy representing an adult male with no cervical spine protection.

FIG. 9(e) is a schematic diagram of a hybrid III dummy representing an adult male wearing football gear.

FIG. 9(f) is a schematic diagram of a hybrid III dummy representing an adult male wearing football gear and an exemplary cervical spine protection apparatus of the present invention.

FIG. 10(a) is a schematic showing the effect of on the head and cervical spine of an adult male that is unprotected, wearing football gear and wearing both football gear and an exemplary cervical spine protection apparatus of the present invention at the start of flexion.

FIG. 10(b) is a schematic showing the effect of maximum flexion on the head and cervical spine of an adult male that is unprotected, wearing football gear and the same individual wearing both football gear and an exemplary cervical spine protection apparatus of the present invention.

DETAILED DESCRIPTION OF THE PREFERRED EMBODIMENTS

Figure 1A:
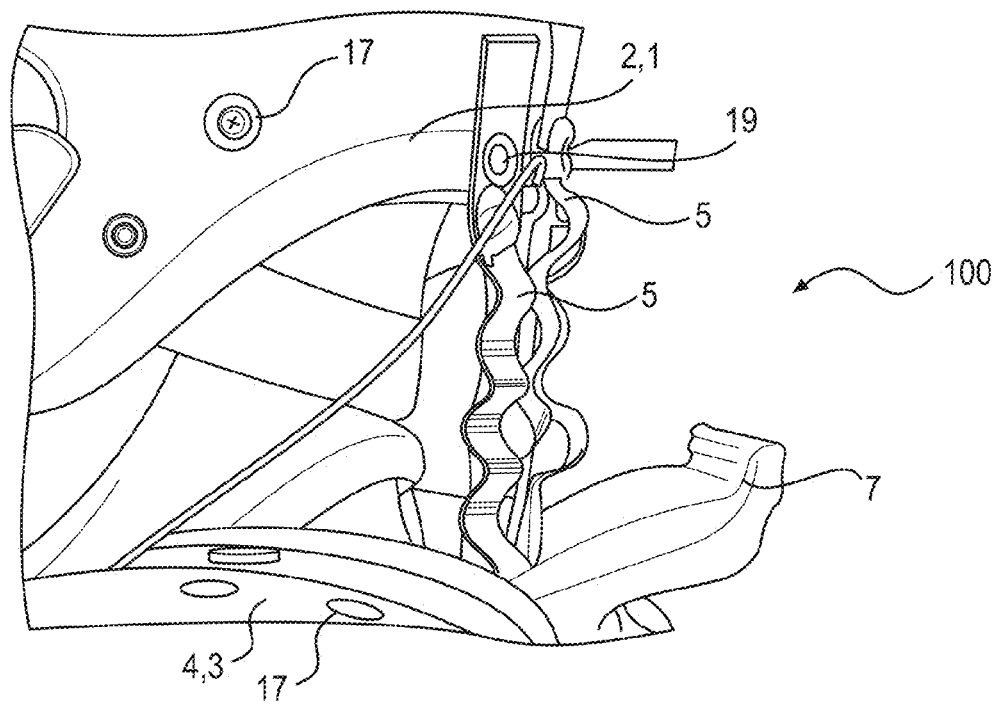
FIG. 1(a) is a sagittal view of an exemplary embodiment of the invention, wherein a user's head is in a neutral position.
Figure 1B:
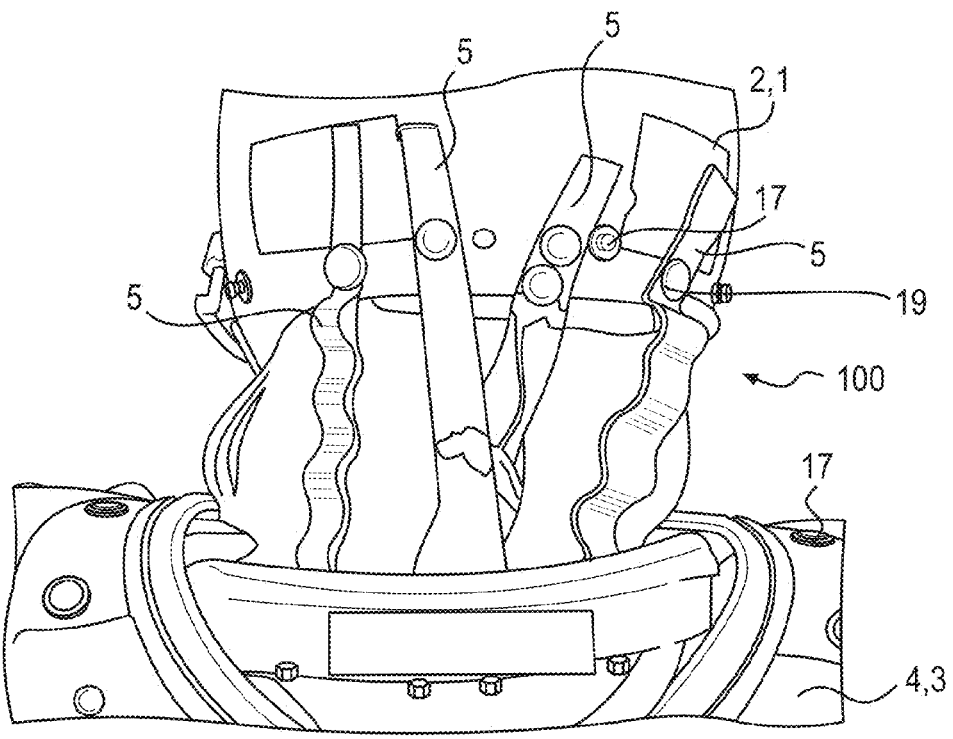
FIG. 1(b) is a posterior view of the embodiment of FIG. 1, wherein the user's head is in a neutral position.
Figure 1C:
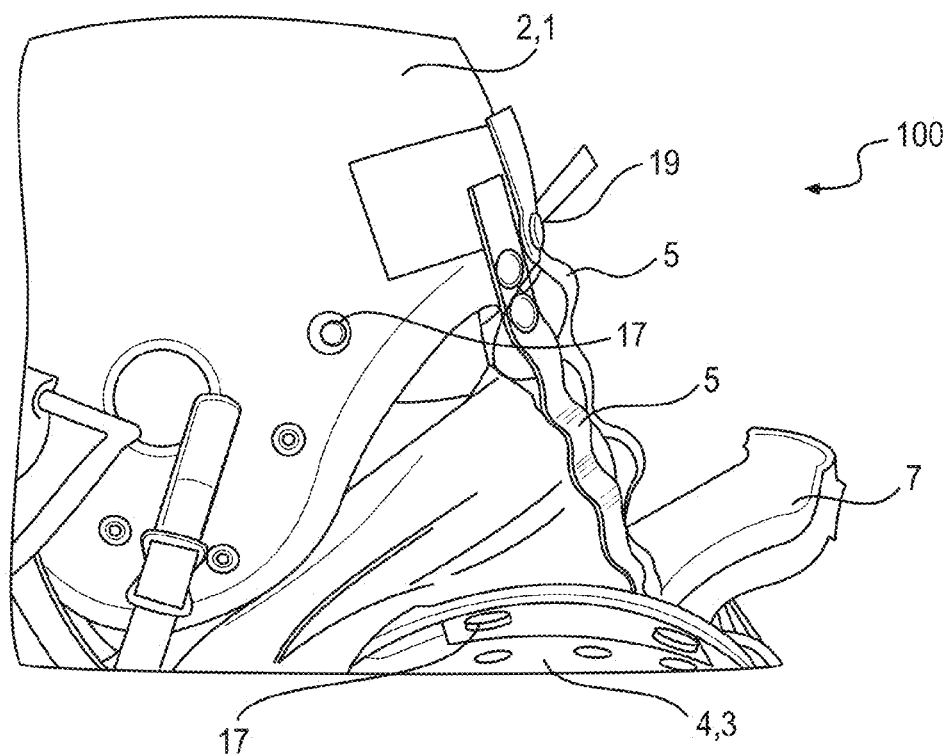
FIG. 1(c) is a perspective view of the embodiment of FIG. 1, wherein the user's cervical spine is flexed.
Figure 1D:
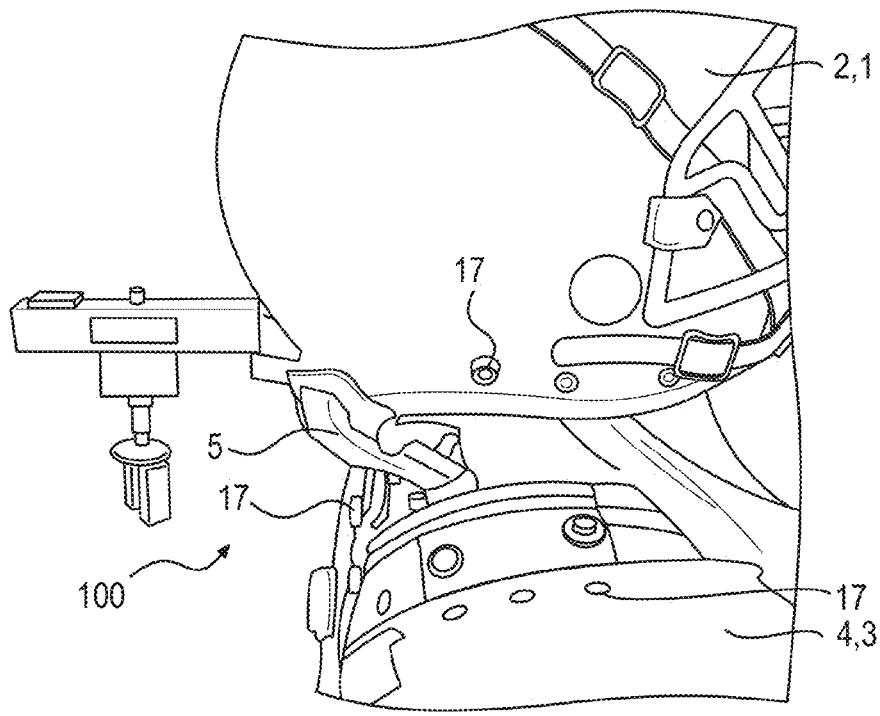
FIG. 1(d) is a side view of the embodiment of FIG. 1, wherein the user's cervical spine is extended.
Figure 1E:
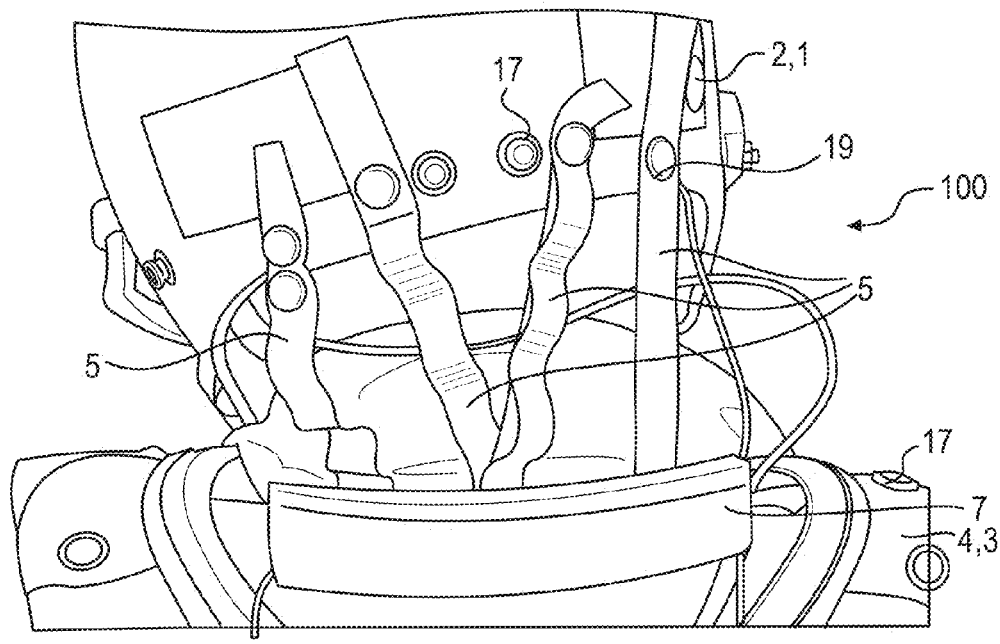
FIG. 1(e) is a rear view of the embodiment of FIG. 1, wherein the user's cervical spine is bent laterally.
Figure 1F:
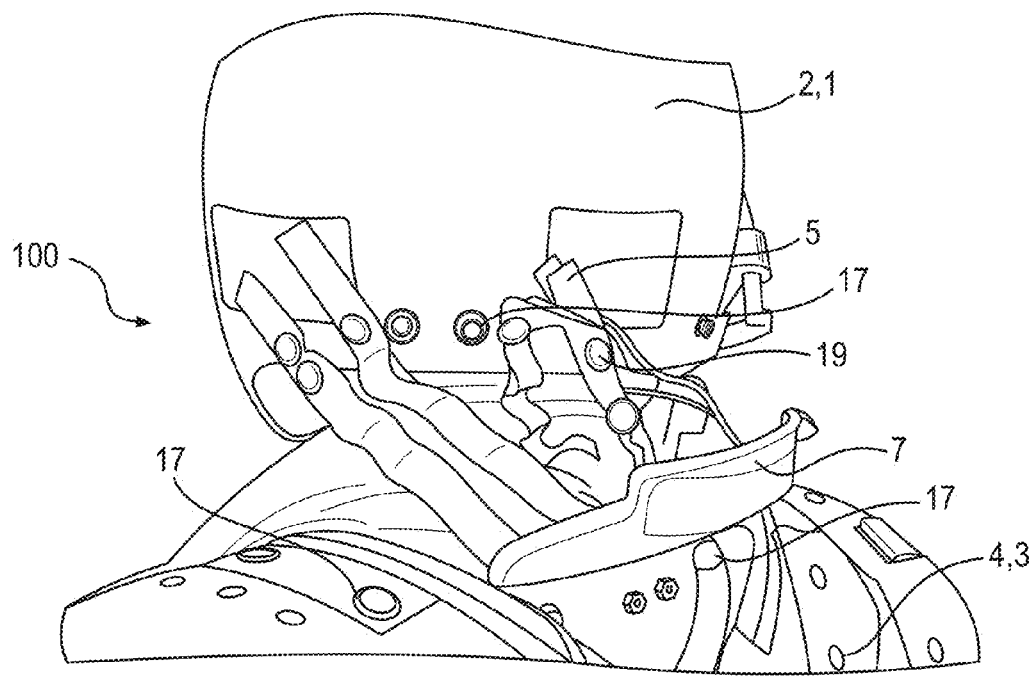
FIG. 1(f) is a perspective view of the embodiment of FIG. 1, wherein the user's cervical spine is rotated about its axis.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Thus, for example, reference to "a spring" may include a plurality of springs and equivalents thereof known to those skilled in the art, and so forth. As well, the terms "a" (or "an"), "one or more" and "at least one" can be used interchangeably herein. It is also to be noted that the terms "comprising", "including", "composed of" and "having" can be used interchangeably.

The present invention is directed to a novel spinal protection apparatus and methods for spinal stabilization. In an exemplary embodiment, the invention may substantially facilitate the rehabilitation of or prevent and/or minimize the risk of incurring and/or severity of a spinal injury, particularly a cervical spine injury, by eliminating or minimizing the risk of injury due to hyperextension, rotational hyperextension, flexion, lateral bending and other potentially injurious spinal movements. Cervical spinal protection apparatus 100 of the present invention includes one or more composite bands 5 and functions to restrain a user's head from assuming an injurious position. Apparatus 100 may be attached between one or more upper attachment structures 2 that may be operatively associated with a wearer's head, such as with a portion of a helmet 1, and one or more lower attachment structures 4, such as may be associated with a brace 3 or platform 7 that may be operatively associated with a lower region of the wearer's body. Apparatus 100 of the present invention may be used to protect the cervical spine from injury due to a variety of impact and inertial forces without substantially interfering with the wearer's normal range of motion. It is envisioned that apparatus 100 may be particularly suitable for use as a physical therapy device to facilitate cervical spine rehabilitation or as safety equipment, such as protective athletic gear, protective construction gear, protective mining gear, etc.

Apparatus 100 may be attached to any one or more upper attachment structures 2 operatively associated with the head of a wearer. An exemplary upper attachment structure 2 may be all or a portion of any head gear or structure suitable for securing apparatus 100 to the head of a wearer. In an exemplary embodiment, upper attachment structure 2 may be a portion of or attached to a helmet 1, which may be any suitable head covering that partially or completely covers a user's head. Helmet 1 may have a closed and continuous structure that encloses a user's head, an open framework that exposes one or more portions of the user's head or any combination thereof. Additionally, helmet 1 may be constructed from any material suitable for the intended use, including fabrics, metals, ceramics, polymers, resins, or combinations thereof. Depending upon the application, helmet 1 may be constructed to have a substantially hard or soft outer and/or inner shell. Helmet 1 may also include one or more conventional adjustment mechanisms for ensuring that helmet 1 is adequately secured to a user's head, such as straps, bands, snaps, or other fasteners. Exemplary helmets 1 may include athletic headgear for sports and recreational activities, such as football helmets, hockey helmets, baseball helmets, biking helmets, mountain climbing helmets, skiing helmets, skateboarding helmets, and motorcycle helmets; protective hard hats; protective mining hats; conventional fabric caps; visors; etc.

Apparatus 100 may also be attached to one or more lower attachment structures 4 operatively associated with a region of the user's body lower than the head. In an exemplary embodiment, lower attachment structure 4 may be attached to or provided by one or more braces 3. Brace 3 may have any structure or configuration suitable for providing or attaching one or more substantially fixed attachment structures, such as platforms 7. In an exemplary embodiment, brace 3 may be worn about a user's neck and/or torso, such as the shoulders, back, waist or combinations thereof. Brace 3 may include one or more conventional adjustment mechanisms for ensuring that brace 3 is secured to the user's body, such as straps, bands, snaps, or other fasteners. Exemplary braces 3 may include back braces, neck braces, shoulder pads, shoulder pads bridged with a back panel and/or neck rest, or combinations thereof.

Optionally, the fixed attachment structures may be provided by or associated with one or more platforms 7 that are integrally or removably attached to brace 3. Each platform 7 may have any suitable shape, dimension or configuration for providing the required fixed attachment structures or allowing attachment of suitable attachment structures. As shown in the exemplary embodiment of FIGS. 1(a)-1(f), platform 7 has a substantially planar posterior surface or flange for engaging composite bands 5. Platform 7 may further encircle at least a portion of the user's neck, such as a left side of the neck, posterior region of the neck, right side of the neck or combinations thereof. Platform 7 may optionally further include an upwardly extending flap or collar that may offer further support and protection to the user's cervical spine.

Figure 2A:
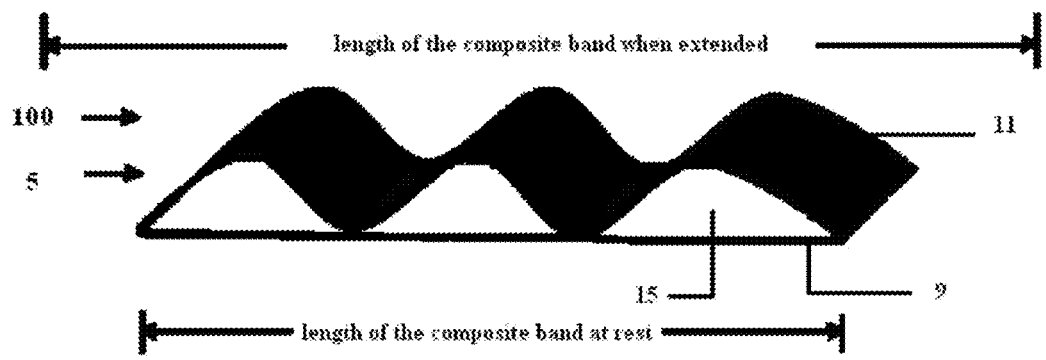
FIG. 2(a) is a perspective cross-sectional view of an exemplary composite band of the invention.
Figure 2B:
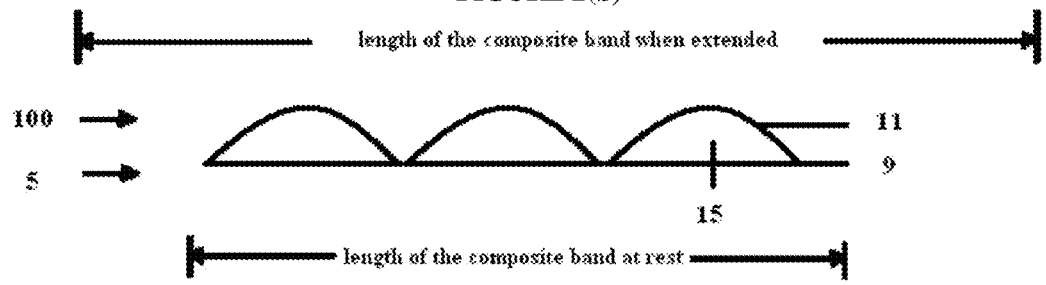
FIG. 2B is a lateral cross-sectional view of the exemplary composite band of FIG. 2(a).

As shown in FIGS. 1(a)-1(f), apparatus 100 includes one or more composite bands 5 that connect between an upper attachment structure 2, such as a portion of helmet 1, to a lower attachment structure 4, such as a portion of brace 3 and/or platform 7. Each composite band 5 is designed to provide non-linear variable flexibility that is dependent upon variations in loading rates As shown in FIGS. 2(a)-2(b), in one exemplary embodiment, composite band 5 is a viscohyperelastic composite band which includes one or more elastic bands 9 having a low modulus of elasticity and one or more substantially non-extendable bands 11 having a high modulus of elasticity that attaches to one another using any conventional fastening means, such as by stitching, adhesive, heat fusion or combinations thereof. Bands 9, 11 may be attached to one another either partially or along the entire lengths of bands 9, 11 to form an integral structure. Elastic band 9 may be constructed from any elastic or spring like material that is suitable for providing the desired elasticity of band 9, and substantially non-extendable band 11 may be constructed from any substantially non-extendable and/or non-stretchable material.

In an exemplary embodiment, elastic band 9 may be constructed from one or more elastic fabrics or polymers, such as rubber or nylon, elastic fabrics including Kevlar™ fibers, a spring such as a metal spring, or combinations thereof. The elastic fabrics are preferably embedded in the elastic band in a crimped pattern to provide the desired elastic properties. Elastic band 9 may have a modulus of elasticity of about 20 psi to about 30,000 psi.

Exemplary materials for constructing substantially non-extendable band 11 may include one or more substantially non-extendable fabrics or polymers, such as stiff canvas, a spring such as a metal spring or combinations thereof. Substantially non-extendable band 11 may have a modulus of elasticity of about 400,000 psi to about 7,500,000 psi.

Elastic band 9 and substantially non-extendable band 11 may have any configuration suitable for enabling the viscohyperelastic flexibility and extension of composite band 5. For example, elastic band 9 and/or substantially non-extendable band 11 may have a coiled spring structure, leaf spring structure, planar band structure, undulating wave structure or any suitable combination thereof. In the exemplary embodiment shown in FIGS. 2(a)-2(b), elastic band 9 may be configured as a flexible planer band, and substantially non-extendable band 11 may have a wavy configuration.

Figure 2C:
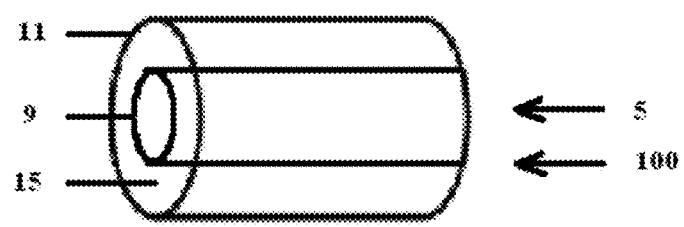
FIG. 2(c) is a perspective cross-sectional view of another exemplary composite band of the invention having a cylindrical configuration.
Figure 2D:
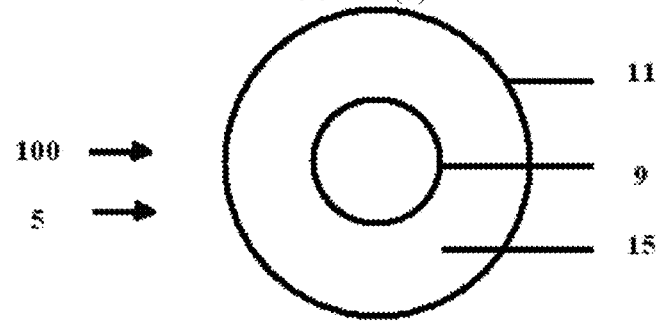
FIG. 2(d) is a longitudinal cross-sectional view of the exemplary composite band of FIG. 2(c).

FIGS. 2(c)-2(d) show another exemplary embodiment, wherein elastic band 9 and substantially non-extendable band 11 together form a cylindrical configuration. Optionally, elastic band 9 and substantially non-extendable band 11 may be surrounded by a sleeve 13 that may be fabricated from any material that accommodates and does not interfere with the movement or flexibility of elastic band 9 and substantially non-extendable band 11.

Optionally, as shown in FIG. 2(a)-2(d), the area between elastic band 9 and substantially non-extendable band 11 may be partially or completely filled with a viscous material 15 suitable for facilitating dampening of the movement of the visco-hyperelastic composite band 5. Exemplary viscous materials may be any gel having a viscosity similar to oil, grease or polymers, such as nylon. Preferably, the viscous material has a viscosity of about 150 cP to about 100,000 cP.

In an exemplary embodiment, viscous material 15 may maybe contained between elastic band 9 and substantially non-extendable band 11 by virtue of the attachment between these bands 9, 11. In one embodiment, elastic band 9 and substantially non-extendable band 11 may be attached to one another along the perimeters of the bands and viscous material 15 may freely flow therebetween. In another embodiment, elastic band 9 and substantially non-extendable band 11 may be attached to one another along the perimeter of the bands and between each wave of the substantially non-extendable band 11 so as to form a plurality of pockets therebetween that may individually contain viscous material 15. Alternatively, viscous material 15 may be contained within sleeve 13 such that it may flow freely within sleeve 13 and between elastic band 9 and substantially non-extendable band 11.

The structure and design of visco-hyperelastic composite band 5 provides motion of the band 5 that mimics the non-linear visco-hyperelastic biomechanics of the connective tissue surrounding the cervical spine, enabling stable unconstrained movement within a normal functional range of motion. Composite bands 5 also provide increased support and stability for the cervical spine at the extreme positions within the normal range of motion and generate resistance to movement of the cervical spine beyond the normal functional range of motion for a particular wearer. Similar to an individual's natural biological system, composite band 5 provides low stiffness at low stretch ratios. The stiffness of band 5 then increases exponentially as the stretch ratio increases.

Since an individual's functional range of motion is highly dependent upon the speed of loading, composite band 5 is designed to account for variations in loading rates by comparatively decreasing the allowed range of motion at high loading rates relative to allowed range of motion at lower loading rates. Furthermore, visco-hyperelastic composite band 5 may also help maintain the head in a neutral, upright position that supports the natural lordotic curve of the cervical spine, assisting the wearer in supporting heavy helmets 1 and/or facemasks as well as acting to prevent the head from assuming an extreme position within the natural range of motion. Therefore, cervical spine protection apparatus 100 substantially protects a user from spinal injuries without substantially compromising the user's normal functional range of motion and by minimizing the magnitude of forces applied to the neck and cervical spine by helping to maintain the head in a neutral, upright and relaxed position.

FIGS. 2(a)-2(b) illustrates the operation of visco-hyperelastic composite band 5. At rest, substantially non-extendable band 11 may assume a natural waveform configuration, wherein no stress is applied by substantially non-extendable band 11 to elastic band 9. As band 5 is stretched, elastic band 9 is held in tension and substantially non-extendable band 11 begins to straighten as both bands lengthen. In this initial stretched state wherein elastic band 9 is under tension and substantially non-extendable band 11 is not yet fully extended from its initial folded state, the combination of elastic band 9 and substantially non-extendable band 11 offers a relatively low resistance to movement. Only the resistance of elastic band 9 is functionally engaged at these low stretch ratios or low applied loads.

As composite band 5 approaches full extension, resistance substantially increases due to the fact that substantially non-extendable band 11 is extended to its full length at which point it becomes non-extendable and offers significant resistance to further movement. Thus, substantially non-extendable band 11 may be used to prevent the user's cervical spine from assuming injurious positions beyond the normal functional range of motion. At these high stretch ratios or high applied loads, substantially non-extendable band 11 becomes substantially engaged, substantially increasing the total resistance of composite band 5. Preferably, composite band 5 is adjusted such that substantially non-extendable band 11 becomes fully extended and straightened when the wearer assumes a position at an extreme of the normal functional range of motion. At this point, visco-hyperelastic composite band 5 becomes several times stiffer than the stiffness of elastic band 9 and generates significant resistance to further motion of the cervical spine.

In embodiments including viscous material 15, viscous material 15 provides the additional benefit of adjusting the resistance offered by composite band 5 relative to the applied loading rate. Thus, as the rate of loading increases, the amount of resistance offered by the viscous material 15 of composite band 5 also increases. Therefore, this aspect of the visco-hyper elastic composite band 5 of the present invention provides additional protection for the cervical spine in the case of high loading rates such as may be encountered during high speed impact. However, viscous material 15 does not substantially alter the resistance provided by elastic band 9 and substantially non-extendable band 11 during lower loading rates.

In an exemplary embodiment, two or more, preferably, four or more visco-hyperelastic composite bands 5 may be used to connect helmet 1 and brace 3 to provide multi-directional protection and reduce the risk and/or severity of incurring cervical spine injuries due to various types of loading and/or impact forces. Visco-hyperelastic composite bands 5 may be arranged in a network or matrix that restricts cervical spine movement to within an optimal or normal range of motion in one or more directions. As shown in the exemplary embodiment of FIGS. 1(b), (e) and (f), four composite bands 5 may be positioned and attached to the posterior region of helmet 1 and brace 3 or platform 7. Alternatively, a distal end of one or more composite band 5 may be positioned on a left side, right side or posterior region of helmet 1 and the corresponding proximal end of one or more composite bands 5 may be attached to a left side, right side or posterior region of brace 3 and/or platform 7. Composite bands 5 may be oriented in different directions relative to one another and oriented at different angles relative to an attachment structure. Depending upon the desired range of motion and degree of resistance desired, composite bands 5 may or may not be arranged to cross paths with other composite bands 5. In an exemplary embodiment, composite bands 5 may be positioned to provide resistance to extension and/or flexion of the cervical spine. Composite bands 5 may also be positioned to provide resistance to lateral movement of the head or to rotation of the spine or head about the axis of the spine. Combinations of composite bands 5 may be employed to resist two or more of these types of motion as well. Further, specific, different composite bands 5 may be employed to resist motion in a particular direction. For example, a system of four bands may be employed to: (1) resist extension flexion, (2) resist lateral movement to the right, (3) resists lateral movement to the left, and (4) resist rotation about the longitudinal axis of the cervical spine.

Composite bands 5 may be integrally or removably attached to one or more upper attachment structures 2, such as may be provided by or attached to a helmet 1, and/or one or more lower attachment structures 4, such as may be provided by or attached to a brace 3, platform 7 or combinations thereof. In one embodiment, helmet 1, brace 3 and platform 7 may include one or more, preferably, two or more fasteners 17 that may facilitate removable attachment of composite bands acting in concert with one or more, preferably, two or more corresponding fastener 19 positioned on, through or in each composite band 5. Exemplary fasteners 17 and corresponding fasteners 19 may include hooks, loops, snaps, threaded means, latches, notches, clasps, apertures, or combinations thereof suitable for removably securing composite band 5 to helmet 1, brace 3, platform 7 or combinations thereof. Alternatively, composite band 5 may be wrapped around, tied about, or may be held in place by a friction fit or form fit to a suitable fastener such as a snap 17, or combinations thereof. Similarly, one or more devices providing upper and lower attachment structures may be wrapped around, tied about, form a friction fit or form fit to a suitable corresponding fastener such as a snap 19, or combinations thereof. As shown in FIGS. 1(a)-1(f), a plurality of fasteners such as snaps 17 and corresponding fasteners such as snaps 19 may be positioned on a surface of or within composite band 5, helmet 1, brace 3, platform 7 or combinations thereof in order to adjust the fit of cervical spine protection apparatus 100 to any user. In an exemplary embodiment, multiple fasteners 17 may be arranged on a left side, right side, posterior region or any combination thereof of helmet 1, brace 3 and/or platform 7. A plurality of corresponding fasteners 19 may be arranged on a distal end, proximal end, or intermediate region therebetween of each composite band 5. Fasteners 17 and corresponding fasteners 19 enable a user to select attachment structures, arrange the location, adjust the length, arrange the orientation or a combination thereof of composite band 5 in order to provide the desired range of motion which may be customized for the particular wearer. Alternatively, composite bands 5 may be integrally attached to helmet 1, brace 3, platform 7 or combinations thereof wherein cervical spine protection apparatus 100 has been manufactured to fit a particular user or a particular size of user.

The invention is also directed to a method for spinal stabilization that involves using cervical spine protection apparatus 100 to reduce and/or minimize the risk and/or severity of incurring cervical spine injuries. Upon putting on cervical spine protection apparatus 100, an upper attachment structure 2, such as may be provided by or attached to helmet 1, may be adjusted to ensure a secure fit with the user's head using any conventional attachment mechanism; similarly, a lower attachment structure 4, such as may be provided by or attached to brace 3, may be adjusted to ensure that it is secured to the user. Composite bands 5 may be attached to helmet 1 and brace 3 and/or platform 7. In the method, one or more of the placement, length and orientation of composite bands 5 may be adjusted for the particular wearer to provide resistance to particular types of movement and/or forces, to customize the apparatus to the user's functional range of motion and to compensate for the possibility of high loading rates in high impact activities such as tackle football.

In an exemplary embodiment, the arrangement of composite bands 5 may be dictated by a computer program stored on a computer readable medium. The computer program may run on a specialized medical diagnostic computer including suitable hardware or software specially designed for medical purposes or alternatively, any conventional computer. Upon inputting various factors, conditions, dimensions, or combinations thereof associated with an intended user and/or application, the program may recommend the number, position, orientation and/or lengths of composite bands 5 to be used. In an exemplary embodiment, the computer program may consider the gender, overall weight, head size, head mass, neck size, neck strength and musculature, shoulders size, shoulder musculature, cervical spine morphology, desired range of motion of the cervical spine, intended activity, intended applied force, previous injuries to the connective tissue of the cervical spine, previous injuries to the cervical spine, helmet size, helmet weight, center of gravity, or combinations thereof when determining the number, positions, orientations and/or lengths of composite bands 5. One or more composite bands 5 may then be attached to helmet 1, brace 3, platform 7 or combination thereof using fasteners 17 and complementary fasteners 19. This ability to adjust cervical spine protection apparatus 100 allows the invention to accommodate for variations between individuals and/or types of activity and provides an effective apparatus that may be used to safeguard the cervical spines of adults as well as that of developing children and adolescents.

In an exemplary embodiment, cervical spine protection apparatus 100 may be used to safeguard and reduce the risk of injuring the cervical spine or the severity of such injuries during any sporting, occupational or recreational activity. In an exemplary embodiment, it may be used to safeguard and reduce the risk and/or severity of cervical spine injury for participants of high impact sports or recreational activities, such as football, hockey, baseball, biking, mountain climbing, skiing and skateboarding. In an exemplary embodiment, the invention may be designed to particularly protect the user from or minimize the risk and/or severity of various multidirectional cervical spine injuries due to injurious movement such as, hyperextension, rotational hyperextension, lateral overextension, flexion, or combinations thereof, without interfering with athletic performance. In an exemplary embodiment, cervical spine protection apparatus 100 may substantially prevent or minimize the risk of assuming an injurious position in two or more different directions or two or more different types of motions, preferably substantially prevent or minimize the risk of assuming an injurious position in three or even four or more different directions or three or four or more different types of motions.

The invention is also directed to a method for using cervical spine protection apparatus 100 of the present invention to facilitate the rehabilitation of any injuries to or deformities of the cervical spine. In an exemplary embodiment, upper attachment structure 2 may be attached to or provided by a conventional hat or scaffold, and lower attachment structure 4 may be attached to or provided by any back brace or neck brace. Upon placing the cervical spine protection apparatus 100 on an individual who has suffered a cervical spine injury or suffers from a cervical spine deformity, apparatus 100 may be adjusted in the same manner as described above. The individual may then participate in supervised physical therapy exercises. Cervical spine protection apparatus 100 may also enable the user to perform physical therapy exercises without supervision while ensuring that the user does not assume a position that would further exacerbate the injury. In an exemplary embodiment, cervical spine protection apparatus 100 may be particularly useful for individuals who have suffered a cervical spine injury prone to recurrence, such as cervical cord neurapraxia. Cervical spine protection apparatus 100 may be used to facilitate healing and prevent and minimize the risk of reinjuring the cervical spine.

EXAMPLES

Example 1

Figure 3A:
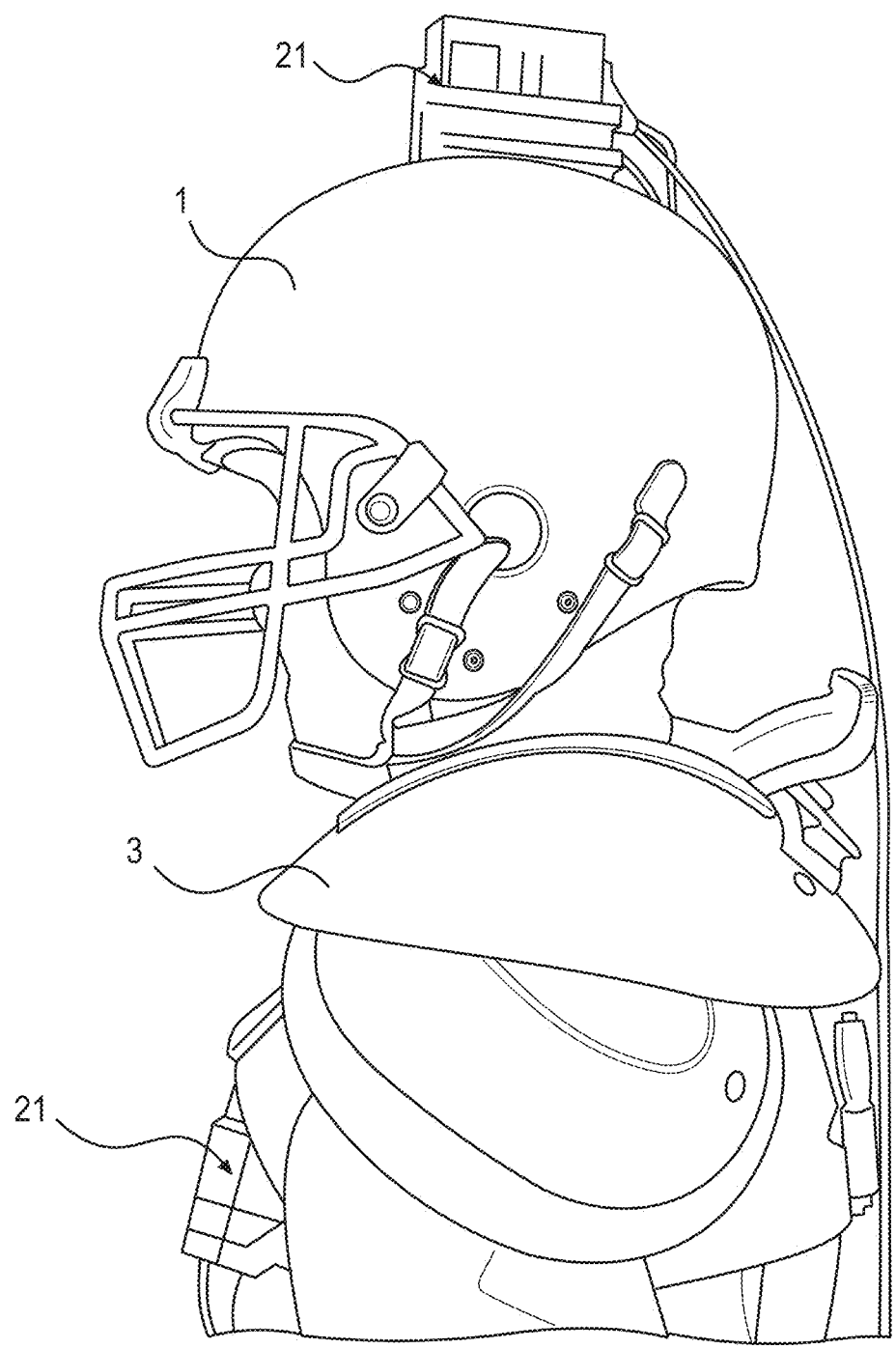
FIG. 3(a) shows a helmet and a brace of the invention showing acceleration, velocity and displacement sensors mounted thereon.
Figure 3B:
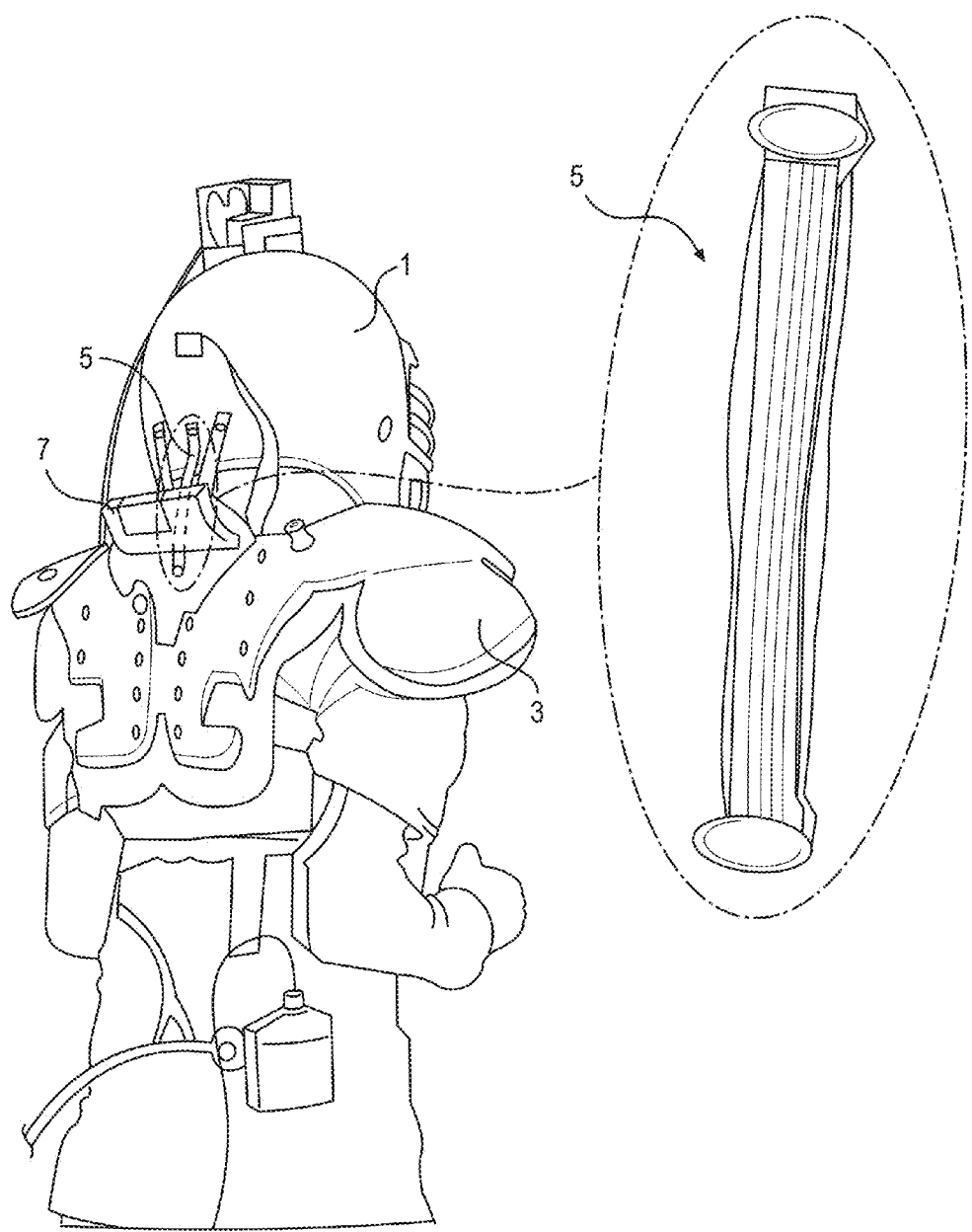
FIG. 3(b) shows an exemplary embodiment of the invention as well as acceleration, velocity and displacement sensors mounted on the wearer for testing the invention.
Figure 4A:
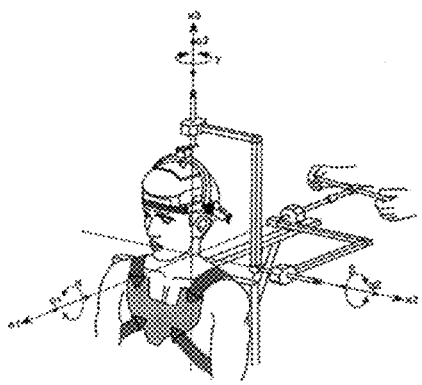
FIG. 4(a) is a schematic diagram of the Neck Flexible Tester (NFT) system for measuring the biomechanical properties of the cervical spine under quasi-static conditions.

An exemplary embodiment of the cervical spine protection apparatus 100 of the present invention was constructed and evaluated to determine its biomechanical capabilities. As shown in FIGS. 1(*a*)-1(*f*), the cervical spine protection apparatus 100 was attached to a standard football helmet 1 and a brace 3 configured as conventional football shoulder pads having a platform 7. Visco-hyper elastic composite bands 5 of apparatus 100 were made from an elastic band 9 stitched to a substantially non-extendable band 11 constructed from stiff canvas cloth. A viscous silly putty material 15, filled the interior cavity formed between elastic band 9 and substantially non-extendable band 11. Four visco-hyper elastic composite bands 5 were removably secured with snaps between football helmet 1 and shoulder pads 3. As shown in FIG. 3(*a*)-3(*b*), strain-gage torque sensors were mounted to football helmet 1 to measure the sagittal plane dynamics, and positional, transitional and rotational sensors were also mounted to shoulder pads 3 to measure acceleration, velocity and position of the user's head and torso.

Two experiments were conducted on two individuals while wearing cervical spine protection apparatus 100. Using a Neck Flexible Tester (NFT), the quasi-static passive and active mechanical properties of cervical spine protection apparatus 100, including the passive and active range of motion, coupled range of motion, load-displacement/flexibility characteristics and isometric muscle strength (IMS), which predicts the applied maximal active torque, were evaluated. The NFT was designed to accommodate large test subjects wearing football gear and thus was constructed from strong materials and large structural elements that enabled the linkages to withstand the large torques generated by the test subject's neck musculature during IMS testing.

In the first experiment, the test subjects were fitted with a helmet, football shoulder pads and a cervical spine protection apparatus 100 and subsequently positioned within the NFT, shown in FIGS. 2(*a*)-(*b*), to determine cervical spine stabilization and the degree of interference with the user's normal cervical spine range of motion. Designed using the Grood and Suntay anatomical coordinate system (J. Biomech. Eng. 105 (1983) 136), the NFT is a unique six-degrees-of-freedom instrument that can measure the rotational and translational motion of the cervical spine produced either voluntarily by a user or in response to external loads applied by an examiner. The applied torque and resulting motion were measured using strain-gage torque sensors and positional rotational and translational sensors mounted on three axes of the linkage. As shown in FIGS. 2(*a*)-(*b*), one end of an NFT linkage was fixed to a chair supporting the test subject, and the other end of the linkage was fixed to the head through either a lightweight test helmet or football helmet 1. Sitting in the NFT chair, the test subject's lumbar spine and scapulae were supported by the back of the chair and the test subject's pelvis was stabilized with a waist belt while the upper thoracic area, i.e. the base of the cervical spine, was stabilized using a padded breast plate. The axes of the NFT are adjustable so they could be aligned with the user's specific anatomy. In this experiment, the axis fixed to the chair, corresponding to the axis for lateral bending of the cervical spine, was adjusted to align with the first thoracic vertebrae. Specifically, the spinous process of the T1 and one axis of the linkage was adjusted to align with T1. With the head level, the axis fixed to the helmet, corresponding to the axial rotation, was adjusted so that it was perpendicular to the Frankfurt horizontal plane, and the helmet was then attached to the NFT. A third floating axis of the NFT did not require any adjustment as it aligned naturally to provide a measurement of cervical spine flexion and extension. Each axis of the linkage was designed to have a specially constructed combination of linear and angular precision potentiometers to measure the angular and linear displacement of the cervical spine about and along each axis. To measure isometric muscle generated torques, strain-gauge torque sensors were mounted permanently on each axis of the linkage. To provide fixation during the IMS testing and coupled range of motion testing, wherein the cervical spine was fixed in one position, such as in extension, while conducting a range of motion test in a given direction, such as lateral bending, each rotational degree of freedom in the NFT was provided with a lock so that the cervical spine could be positioned and fixed in any desired position. A hexagon structure was machined at the end of each axis so that a socket wrench instrumented with a strain-gage torque sensor could be used to manually apply and measure torques around each axis. Voltage outputs from the potentiometers and the torque sensors were fed into an analog-to-digital converter and stored on a computer.

The active and passive range of motion and the IMS were measured in all directions when the test subjects were: (1) in their football gear, (2) wearing helmet 1 including a cervical spine protection apparatus in accordance with the present invention and (3) out of their football gear wearing only a light helmet fixed by the NFT. The active range of motion was measured by instructing the test subject to move his head in flexion, extension, lateral bending and axial rotation to the point of reaching the limits of the range of motion. Passive range of motion and passive load-displacement characteristics were measured by instructing the test subject to relax and then applying a force to the test subject's head. Specifically, the test subject's head was manually moved in slow cyclic movements in all directions. The applied torque was measured using a torque sensor. Passive limitation of motion, defined as the maximum range comfortably tolerated by the subject, was achieved. IMS estimates were then obtained by instructing the test subject to apply a maximal force in resisting the external cyclic movement. The passive range of motion and load-displacement characteristics were then measured using a torque sensor.

Figure 5:
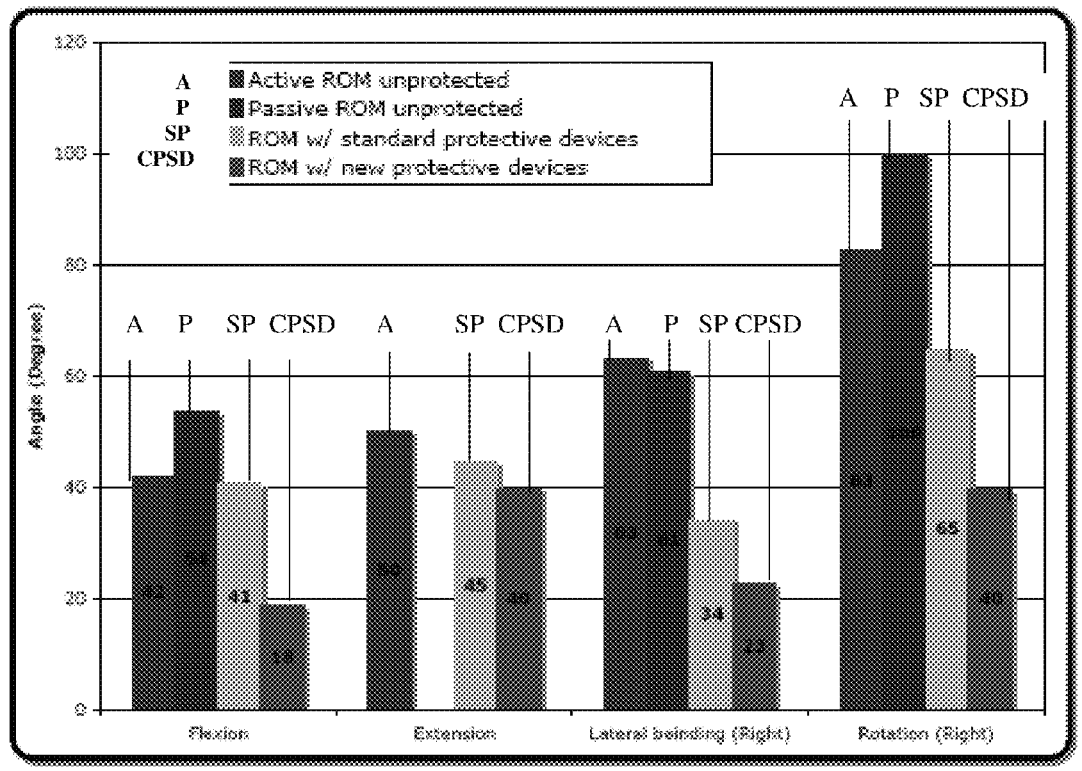
FIG. 5 is a graph of the passive and active range of motion of an individual who was unprotected, wearing football gear and the same individual wearing both football gear and an exemplary cervical spine protection apparatus of the present invention.
Figure 4B:
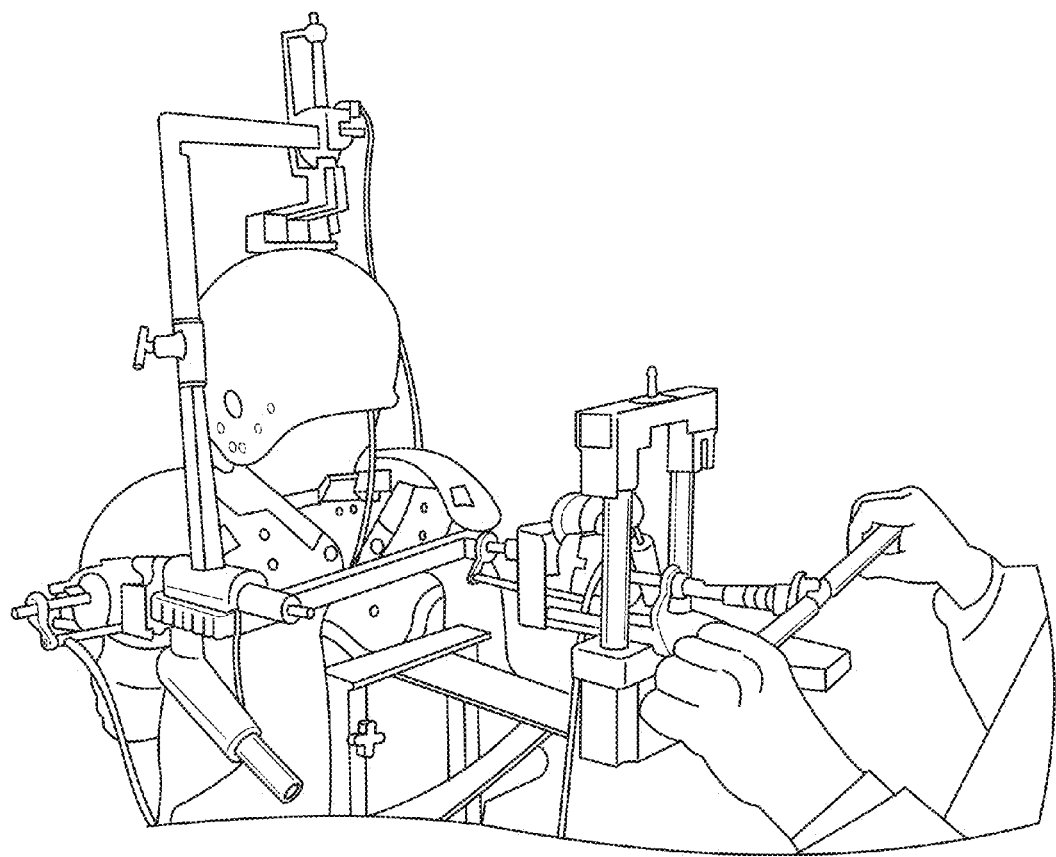
FIG. 4(b) is a photograph of the NFT measuring the cervical spine biomechanical properties of an individual wearing an exemplary cervical spine protection apparatus of the present invention.

As shown in FIG. 5, the test results for the passive and active ranges of motion with and without the football gear revealed that, as expected, the passive range of motion was larger or equal to the active range of motion. Additionally, the football gear significantly limited the range of motion of the cervical spine in lateral bending by 46%. The results demonstrate that apparatus 100 provides multi-directional neck protection without interference with the required functional motion.

In the second experiment, the effect of cervical spine protection apparatus 100 on the dynamics of the cervical spine was evaluated while the test subjects ran on a treadmill at a steady pace of about 1.8 m/s. During the first part of this experiment, each test subject fixated continuously on a visual target at about 3 m distance. In the second part of the experiment, the test subjects ran in the dark. In both scenarios, the test subjects were asked to maintain the head in a comfortable position, facing forward.

To measure the effect of standard football gear and cervical spine protection apparatus 100 on cervical spine dynamic motion in the sagittal plane, sensors that combined a three-axis accelerometer and a three-axis rotational velocity sensor (ADIS16350, Analog Devices, Norwood Mass.) were mounted to the test subject's torso and helmet. Large displacement, indium gallium, strain gages (Hokanson, Bellevue Wash.) were attached from the back of each helmet to the top of the subject's shoulder pads to track head position relative to the trunk. Data was collected using a tablet PC (Motion Computing, Austin Tex.) which was held securely in a backpack worn by the subjects. Testing was conducted under three experimental conditions, wherein the test subjects wore: (1) a lightweight helmet (Petzl Meteor III) only and no shoulder pads; (2) a football helmet (Adams Y-Three) and shoulder pads; and (3) a custom-made cervical spine protection apparatus 100 attached between a football helmet and shoulder pads.

FIG. 6 demonstrates that the football gear pulled the neck into flexion, and that cervical spine protection apparatus 100 positioned between the football helmet and shoulder pads was able to compensate for the weight of a conventional football helmet by pulling the neck and head back into a more natural position and by reducing the neck's angular displacement while the test subject ran. When wearing the lightweight helmet of the NFT, the test subject's head was held back at an angle of about 3.9 degrees relative to the trunk; when running, the angular excursion of the head was positioned at about a root mean square (RMS) value of 2.7 degrees. The head extended back by as much about 13.0 degrees during the experimental trials and was never measured to move more than about 4.1 degrees into flexion. The excursion of the head was similar when the football helmet and facemask were worn, but instead of being centered about an average position of about 3.9 degrees, the position was shifted forward to an average of about 1.0 degree of flexion (RMS 2.7 degrees) and reached as far as about 10.2 degrees into flexion. Cervical spine protection apparatus 100 pulled the head back into extension and reduced the magnitude of the neck's angular motion. The average position of the head was about 1.5 degrees, and the RMS value of the movement was reduced to 1.7 degrees. Results were similar regardless of whether the test subject fixated on a visual target or was tested in the dark.

Accompanying the significant alterations to the position of the head and neck due to the presence of a helmet were changes to the amplitude of the acceleration and velocity of the torso, head and cervical spine. In all cases, however, the predominant frequency of the signals occurred near 3.0 Hz in the sagittal plane (1.5 Hz in yaw) which corresponds to the frequency of the runner's foot strike. Because of the additional mass of the football helmet, the linear acceleration and rotational velocity of the head was lower when wearing the football helmet than without the football helmet. For example, the RMS values of the head's linear acceleration along the x axis (posterior-anterior) decreased approximately 50% from 4.0 m/s$^2$ when the lightweight helmet was worn to about 2.1 m/s$^2$ when the cervical spine protection apparatus 100 was worn. Consistent with decreases in sagittal plane acceleration, the RMS rotational velocity of the head in pitch decreased from about 37.5 deg/s with the lightweight helmet to about 28.1 deg/s with the football helmet, and further to about 20.1 deg/s with the cervical spine protection apparatus 100.

The football helmet impacted the dynamics of the torso as well, despite the fact that the test subject ran on a treadmill at the same speed for each experimental trial. Most interesting was how linear accelerations along the x-axis were affected, as shown in FIGS. 7(a)-(b). The frequency content of the linear accelerations was substantially the same whenever the test subject wore the football helmet. Like football helmets, power for the lightweight helmet was concentrated at the frequency of the foot strike (3.2 Hz) but its spectrum indicated that there was also significant power at harmonic frequencies. In contrast to the frequency spectrum, the amplitude distribution for the subjects wearing the lightweight helmet; football helmet; and cervical spine protection apparatus 100 attached to a football helmet and shoulder pads were much the same, whereas the amplitude distribution for the football helmet alone was different.

The RMS linear acceleration of the trunk doubled from 0.9 m/s$^2$ for the lightweight helmet and from 1.0 m/s$^2$ for the cervical spine protection apparatus 100 to 2.1 m/s$^2$ for the football helmet. This may be attributable to a change in gait that was caused by the football helmet pulling the head and neck forward, and which was corrected by cervical spine protection apparatus 100. As with the head, the RMS rotational velocity of the torso in pitch decreased when the football helmet was worn; from about 85.6 deg/s without the helmet to approximately 45.0 deg/s whenever the football helmet was worn. The changes in the accelerations and velocities of the torso and head caused large changes to the resultant sagittal plane velocity of the cervical spine. The magnitudes of the velocities were largest when the subject wore the lightweight helmet (RMS 136.5 deg/s), much smaller when the football helmet was worn (RMS 76.8 deg/s), and smaller still when cervical spine protection apparatus 100 was worn (RMS 66.0 deg/s). As shown in FIG. 8, the smaller rotational velocities of the head and cervical spine when the football helmet was worn did not result in smaller angular displacements of the cervical spine. The angular displacement of the cervical spine in the sagittal plane was only reduced when cervical spine protection apparatus 100 was worn. Results were similar whether the subject fixated on a visual target or was tested in the dark. Overall, cervical spine protection apparatus 100 exceeded performance expectations, maintaining the neck in an erect posture during running and delayed the onset of neck muscle fatigue.

Example 2

In this computer model study, the difference in the response of a pediatric cervical spine to external loads in comparison to an adult cervical spine, both without and with cervical spine protection apparatus 100, were evaluated. Numerical models of a standard Hybrid III 6-year-old dummy and the standard Hybrid III 50$^{th}$ percentile male dummy were used in simulations conducted using the MADYMO software [TNO, 2004]. These dummies, and similar anthropometric models, are widely used in the automotive and aviation industry for injury risk assessment. Virtual sensors were used to measure the three dimensional linear acceleration of the head and the resultant forces and moments in the upper (at the C1 level) and lower (at the C7 level) cervical spine. FIGS. 9(a)-(g) illustrate the initial setup for the models with no protection, with regular football gear and with cervical spine protection apparatus 100 attached between a football helmet and shoulder pads.

In these simulations, the dummy's head was subject to impact accelerations recorded experimentally on adult tackle football players [Viano, 2005b]. The upper and lower cervical spine force and moment for which are illustrated in FIGS. 10(a)-(b), and the resultant quantitative dynamics, including cervical spine motion, are shown in Table 1 below. The results demonstrate differences between the response of the child's cervical spine from that of an adult as well as the restraining effect of cervical spine protection apparatus 100, which was confirmed experimentally.

TABLE 1

Output parameters produced in the various models in response to an experimental impact acceleration profile.

| Dummy Type | Protection Condition | Head Acceleration (m/sec^2) | Upper Neck Resultant Force (N) | Upper Neck Torque (Nm) | Lower Neck Resultant Force (N) | Lower Neck Torque (Nm) |
|---|---|---|---|---|---|---|
| Hybrid III 6 year old child dummy | No protection | 142 | 1610 | 72 | 1450 | 60 |
|  | With standard protection | 165 | 2106 | 94 | 1980 | 81 |
|  | With CSPD | 142 | 1724 | 64 | 1502 | 48 |
| Hybrid III Adult male dummy | No protection | 87 | 410 | 38 | 451 | 58 |
|  | With standard protection | 93 | 800 | 44 | 884 | 71 |
|  | With CSPD | 75 | 350 | 20 | 415 | 50 |

Example 3

Figure 11:
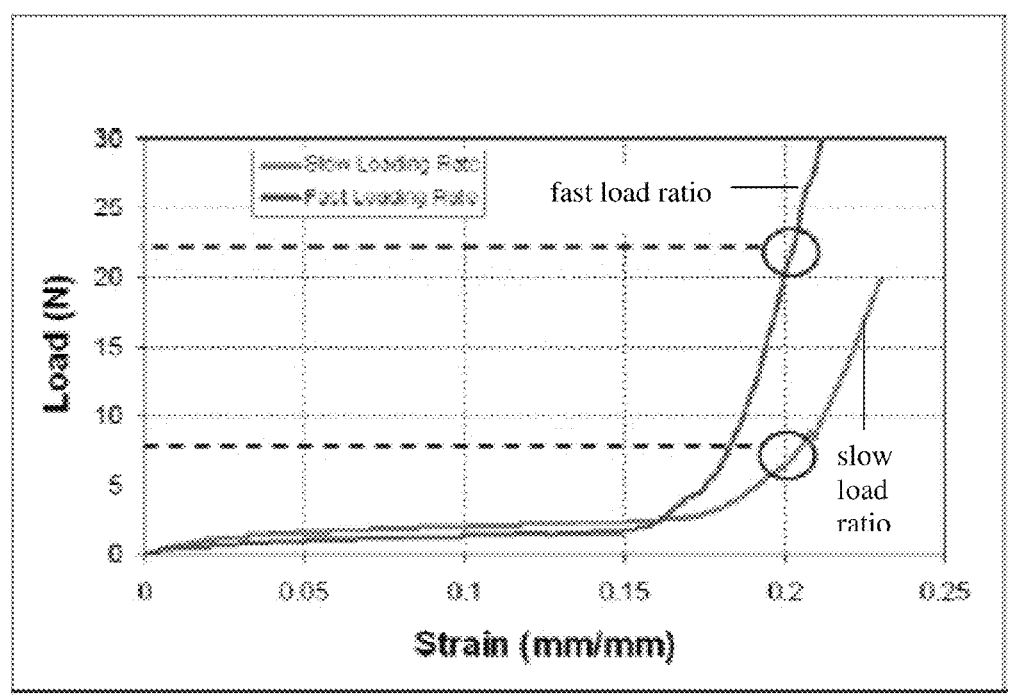
FIG. 11 is a graph of load as a function of strain for an exemplary composite band of the invention showing the behavior of the composite band at slow and fast loading rates.

FIG. 11 shows the results of a tensile test conducted on an exemplary visco-hyperelastic composite band 5 at two different loading rates. The composite band 5 included a elastic band 9 stitched to a substantially non-extendable band 11 constructed from stiff canvas cloth. A viscous silly putty material 15 filled the interior cavity formed between elastic band 9 and substantially non-extendable band 11. FIG. 11 demonstrates that the stiffness of composite band 5 increases dependent on the loading rate of said composite band 5.

Example 4

Figure 12A:
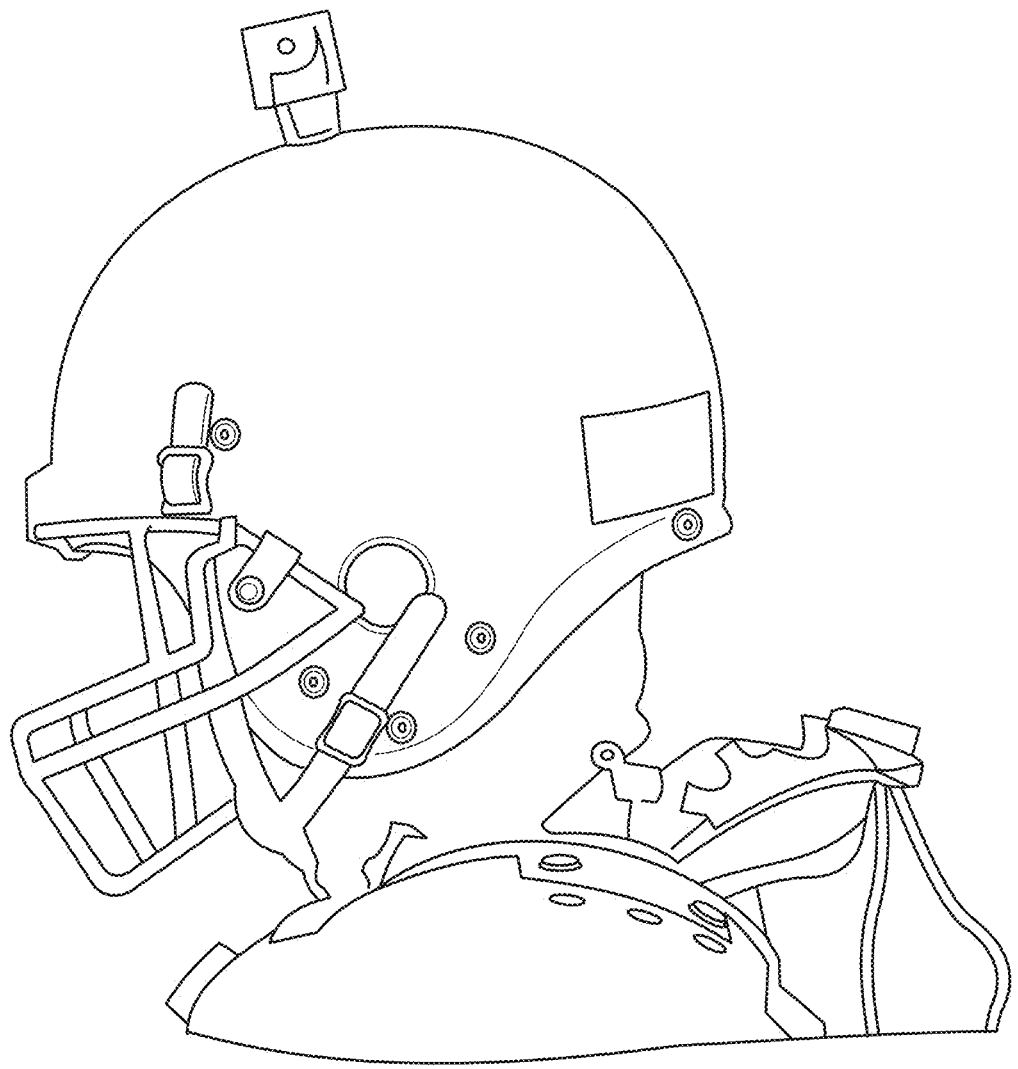
FIG. 12(a) is a side view of a brace before attaching the composite bands of an exemplary cervical spine protection apparatus.
Figure 12B:
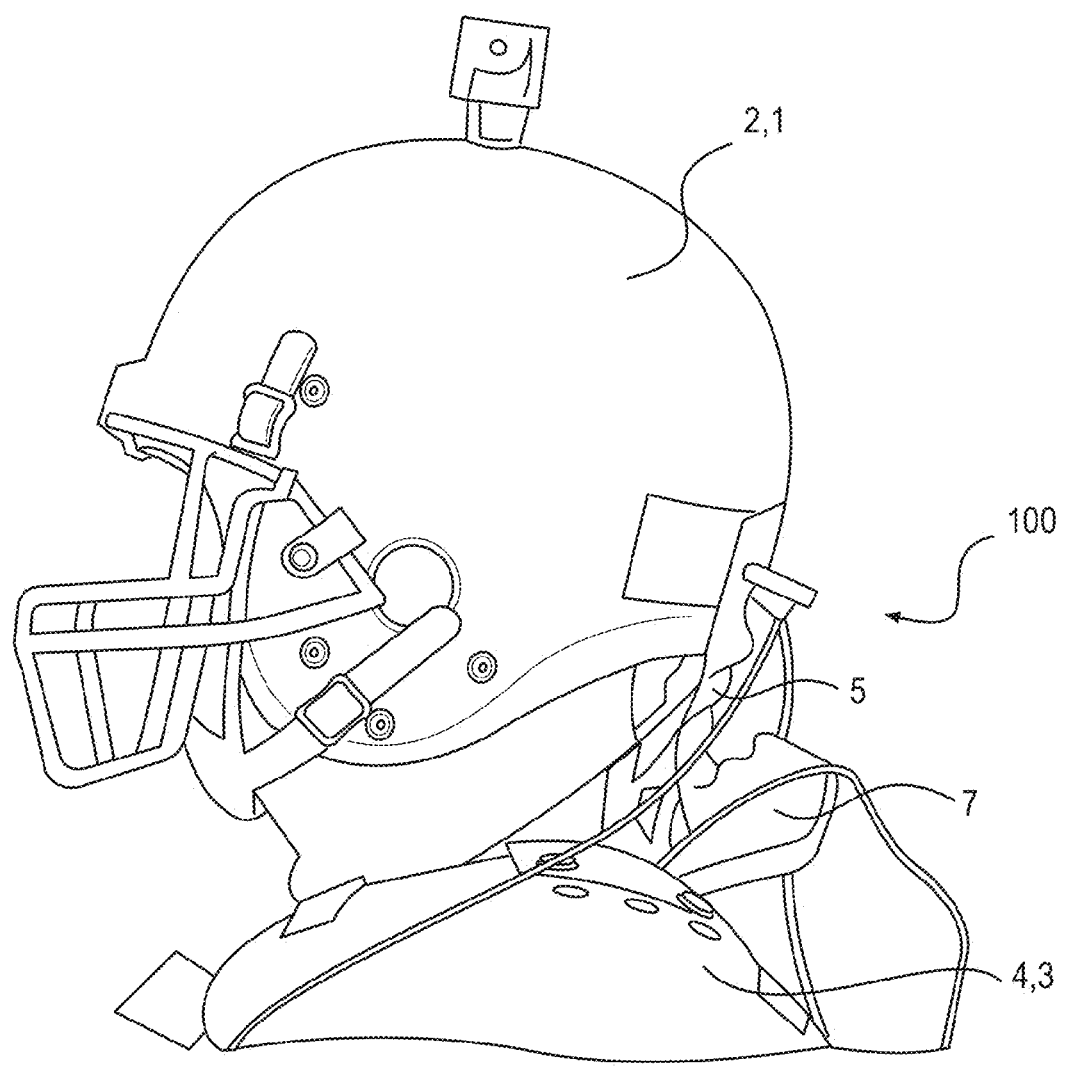
FIG. 12(b) is a side view of an exemplary cervical spine protection apparatus after attaching the composite bands.
Figure 12C:
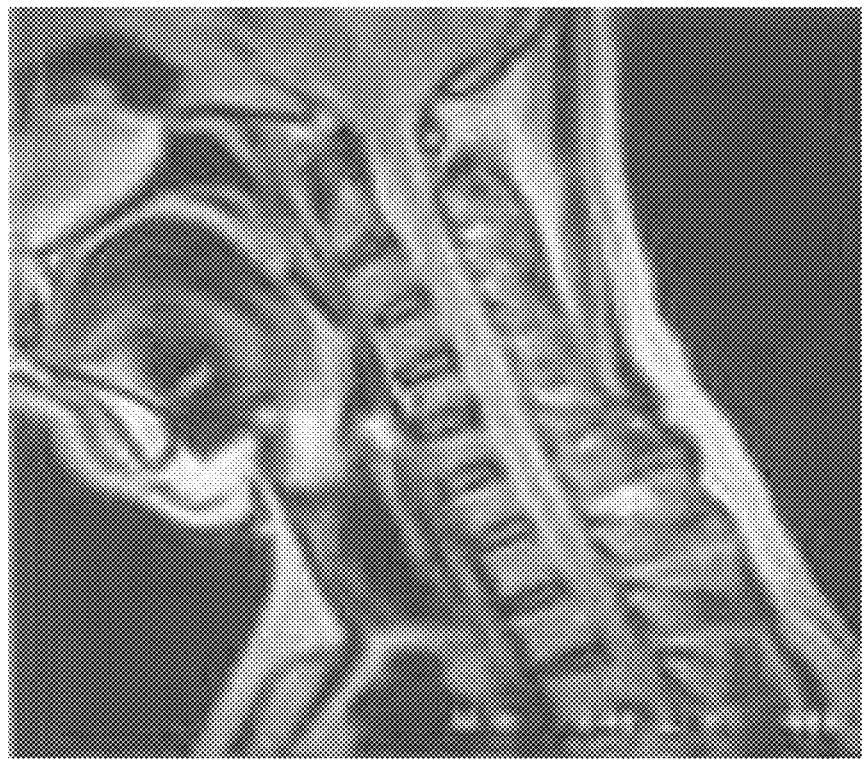
FIG. 12(c) is a magnetic resonance image showing an individual's head in a flexed position without the cervical spine protection apparatus of the invention.
Figure 12D:
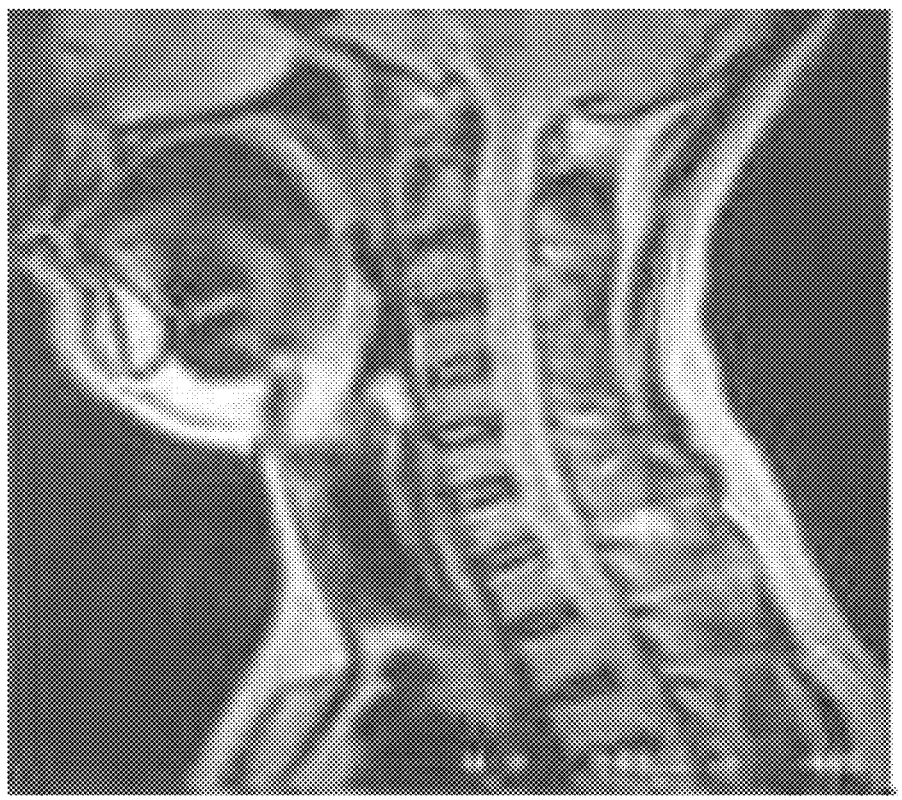
FIG. 12(d) is a magnetic resonance image showing an individual's head in a neutral position when the individual is wearing an exemplary cervical spine protection apparatus of the present invention.

The affect of cervical spine protection apparatus 100 on the position and orientation of a user's cervical spine was also examined. FIG. 12(a) shows the natural head posture of an individual wearing football gear. FIG. 12(b) shows the natural head posture of an individual wearing cervical spine protection apparatus 100 attached to a football helmet and shoulder pads. The visco-hyper elastic composite band 5 of cervical spine protection apparatus 100 functions to support the natural lordotic curve of the cervical spine and aid the neck muscles in supporting the weight of a helmet so that the neck does not move into the flexed posture of FIG. 12(a). FIGS. 12(c)-12(d) compare the MRI images of an individual wearing a football helmet and shoulder pad and the same individual wearing cervical spine protection apparatus 100 attached therebetween, respectively. The MRI images demonstrate the cervical spine protection apparatus 100 prevents the undesirable flexed resting posture in which the cervical spine is axially aligned. Rather, the invention assists the user in maintaining an upright posture with natural lordosis, wherein the neck is curved naturally so forces can be absorbed by musculature rather than by straining ligaments or being transmitted along vertebral bodies.

The foregoing description of the invention has been presented for the purpose of illustration and description only and is not to be construed as limiting the scope of the invention in any way. The scope of the invention is to be determined from the claims appended hereto.

The invention claimed is:

1. A spinal protection apparatus comprising:
a composite band comprising:
an elastic band having a modulus of elasticity of from about 20 psi to about 30,000 psi; and
a substantially non-extendable band having a modulus of elasticity of from about 400,000 psi to about 7,500,000 psi attached to said elastic band in a manner whereby in a rest position of said composite band there is sufficient slack in said substantially non-extendable band to permit said elastic band to stretch a distance which defines a range of motion for a wearer of said composite band.

2. The apparatus of claim 1, wherein a stiffness of said composite band has a non-linear relationship with respect to the loading rate of said composite band.

3. The apparatus of claim 1, wherein said composite band has a lower stiffness upon application of a first loading rate relative to a stiffness of said composite band upon application of a second, faster loading rate.

4. The apparatus of claim 1, wherein said composite band further comprises a non-solid viscous material positioned between said elastic band and said substantially non-extendable band.

5. The apparatus of claim 4, wherein said viscous material has a viscosity of from about 150 cP to about 100,000 cP.

6. The apparatus of claim 1, wherein said apparatus comprises a plurality of composite bands and each said composite band is oriented in a different direction.

7. The apparatus of claim 1, further comprising a first structure providing a first attachment point for attachment of a distal portion of said composite band and a second structure providing a second attachment point for attachment of a proximal portion of said composite band.

8. The apparatus of claim 7, wherein said first structure comprises a helmet.

9. The apparatus of claim 8, wherein said second structure comprises a brace.

10. The apparatus of claim 9, comprising a plurality of composite bands oriented in different directions and wherein each of said helmet and said brace comprises two or more fasteners and wherein said composite band comprises two or more corresponding fasteners suitable for removably attaching said composite band to said helmet and said brace.

11. The apparatus of claim 10, wherein said composite band further comprises fasteners which permit adjustment of a length of said composite band between said helmet and said brace.

12. The apparatus of claim 10, wherein said composite band further comprises a sheath surrounding said elastic and substantially non-extendable bands and a viscous material having a viscosity of from about 150 cP to about 100,000 cP located within said sheath.

13. The apparatus of claim 11, wherein said fasteners are selected from the group consisting of: hooks, loops, snaps, threaded means, latches, notches, clasps, apertures, and combinations thereof.

14. A method for spinal stabilization comprising the steps of:
attaching at least one composite band comprising:
an elastic band having a modulus of elasticity of from about 20 psi to about 30,000 psi; and
a substantially non-extendable band having a modulus of elasticity of from about 400,000 psi to about 7,500,000 psi attached to said elastic band;
to first and second attachment structures located at different positions along a spine in a manner whereby in a rest position of said attached composite band there is sufficient slack in said substantially non-extendable band to permit said elastic band to stretch a distance which defines a range of motion along a longitudinal axis of said elastic band for a wearer of said composite band.

15. The method of claim 14, wherein at least two composite bands are attached in a manner whereby said composite bands are oriented in at least two different directions.

16. The method of claim 14, wherein said at least one composite band is attached in a manner which limits a movement selected from the group consisting of: hyperextension, rotational hyperextension, flexion, lateral movement and combinations thereof.

17. The method of claim 16, wherein a distal portion of the composite band is attached to a helmet and a proximal portion of the composite band is attached to a brace.

18. The method of claim 14, wherein placement of said one or more composite bands is determined by considering one or more factors selected from the group consisting of: gender, weight, head size, head mass, neck size, neck strength and musculature, shoulders size, shoulder musculature, cervical spine morphology, desired range of motion of a cervical spine, intended activity, intended applied force, previous injuries to a connective tissue of a cervical spine, previous injuries to a cervical spine, helmet size, helmet weight and center of gravity of an intended wearer of said apparatus.

19. The method of claim 18, wherein a length of said composite band between a first attachment structure and a second attachment structure is determined by considering one or more of said factors.

20. The method of claim 14, wherein said composite band further comprises a viscous non-solid material located between said elastic band and said substantially non-extendable band.

21. The method of claim 14, wherein said at least one composite band is attached to a wearer that has previously incurred a cervical spine injury and wherein said wearer performs physical therapy exercises while wearing said at least one composite band.

* * * * *